United States Patent [19]

Ishii et al.

[11] Patent Number: 5,179,000
[45] Date of Patent: Jan. 12, 1993

[54] METHOD FOR ASSAYING BASIC FETOPROTEIN IN URINE AND ASSAY KIT THEREFOR

[75] Inventors: Masaru Ishii, Saitama; Yuko Seino, Tokyo, both of Japan

[73] Assignee: Nippon Kayaku Kabushiki Kaisha, Tokyo, Japan

[21] Appl. No.: 591,668

[22] PCT Filed: Jul. 20, 1988

[86] PCT No.: PCT/JP88/00725
§ 371 Date: May 8, 1989
§ 102(e) Date: May 8, 1989

[87] PCT Pub. No.: WO89/01163
PCT Pub. Date: Feb. 9, 1989

Related U.S. Application Data

[63] Continuation of Ser. No. 345,542, May 8, 1989, abandoned.

[30] Foreign Application Priority Data

Jul. 24, 1987 [JP] Japan ................... 62-184920

[51] Int. Cl.$^5$ .................. G01N 33/574; G01N 33/53; G01N 33/48
[52] U.S. Cl. ...................... 435/7.23; 435/7.1; 435/7.2; 435/7.9; 435/7.92; 436/518; 436/64; 436/813
[58] Field of Search ................ 436/548, 518, 64, 813; 435/810, 7.1, 7.23, 7.9, 7.2, 7.92

[56] References Cited

U.S. PATENT DOCUMENTS 4,152,410  5/1979  Ishii ......................... 424/1
4,376,110  3/1983  David et al. ................ 436/548
4,692,404  9/1987  Ashihara et al. ............ 435/5
4,868,106  9/1989  Ito et al. ................... 435/7

FOREIGN PATENT DOCUMENTS 0045103  2/1982  European Pat. Off. .
0140242  5/1985  European Pat. Off. .
0144176  6/1985  European Pat. Off. .
2133146  7/1984  United Kingdom .

OTHER PUBLICATIONS

Nagata et al., "The Role of Basic Fetoprotein in the Field of Urology, with Special Reference to its Value as a Testicular Marker", Hiriyokika Kiyo; 28(10): 1213-1219-Abstract 1982.

Nakazono et al., Nishinihon Journal of Urology, vol. 49, No. 6, 1987, "Evaluation of Tumor Markers in Urogenital Malignancies", (1745-1749).

Chemical Abstracts, vol. 98, May 23-Jun. 6 (1983) p. 316.

Primary Examiner—Esther L. Kepplinger
Assistant Examiner—Toni R. Scheiner
Attorney, Agent, or Firm—Nields & Lemack

[57] ABSTRACT

The present invention provides a method for assaying basic fetoprotein in urine comprising an antigen-antibody reaction with the use of anti-basic fetoprotein antibodies, and an assay kit used for performing said method comprising a first anti-basic fetoprotein antibody, a marker second anti-basic fetoprotein antibody, a solid phase and a standard basic fetoprotein antigen, characterized in that the first antibody and the second antibody react with antigenic determinants different from each other.

5 Claims, 2 Drawing Sheets

Results obtained by assaying BFP in serum and urine of healthy donors and patients with benign urosis.

Results obtained by assaying BFP in serum and urine of patients with urogenital cancers.

METHOD FOR ASSAYING BASIC FETOPROTEIN IN URINE AND ASSAY KIT THEREFOR

This application is a continuation of application Ser. No. 345,542, filed May 8, 1989, now abandoned.

TECHNICAL FIELD

This invention relates to a method for assaying basic fetoprotein and an assay kit therefor.

BACKGROUND ART

Basic fetoprotein (referrred to hereinafter as "BFP"), which is a known basic protein, has been found by one of the inventors of this application in serum, intestine and brain tissues of human fetus. It has been particularly called basic fetoprotein since it is basic in contrast to the known acidic fetoprotein. Furthermore, one of the inventors has established a radioimmunoassay system of said protein and found that the assay of said protein in serum would help to diagnose cancer and judge its condition and therapeutical effect thereon. In particular, it has been found that said fetoprotein is useful to examine the presence of cancer, differing from alpha-fetoprotein (referred to hereinafter as "AFP") which is useful to diagnose cancer of a particular organ.

The following references (1) to (7) may be cited for the above prior findings.

(1) Ishii, M. et al.: Studies on Feto-Neoplastic Antigen. Proceedings of The Japanese Cancer Association, The 34th Annual Meeting, p.173 (1975).

(2) Ishii, M.: Studies on novel basic fetoprotein found in various malignant tumors. Igaku no Ayumi (The Stride of Medicine), 100(3), 344-346 (1977).

(3) Ishii, M.: Basic fetoprotein. Igaku no Ayumi (The Stride of Medicine), 106(5), 273-281 (1978).

(4) Ishii, M.: A new carcinoembryonic protein characterized by basic property. Scand. J. Immunol., 8(Suppl.8), 611-620 (1978).

(5) Ishii, M.: Characterization of basic fetoprotein and clinical usefulness of BFP for immunodiagnosis of human cancer. Carcino-Embryonic Proteins. Chemistry, Biology, Clinical Applications, Vol. 1, Lehmann, F.-G. (ed.), Elsevier/North-Holland Biomedical Press, Amsterdam, 333-340 (1979).

(6) Ishii, M., Nishimura, K., Hattori, M., Kanda, Y. and Ishihara, A.: Postoperative surveillance in patients with stomach cancer and monitoring of immuno-and polychemotherapy in patients with leukemia by basic fetoprotein. Carcino-Embryonic Proteins. Chemistry, Biology, Clinical Applications, Vol. 2, Lehmann, F.-G. (ed.), Elsevier/North-Holland Biomedical Press, Amsterdam, 603-606 (1979).

(7) Ishii, M.: Clinical usefulness of basic fetoprotein for immunodiagnosis of human cancer. Compendium of Assay for Immunodiagnosis of Human Cancer. Development in Cancer Research, Herberman, R. B. (ed.), Vol. 1, Elsevier/North-Holland Biomedical Press, New York, 45-50 (1979).

(8) PROCEEDINGS, Sixth Annual Meeting of the Tumor Marker, Program Abstract, p.111, Oct. 20 (1986), Sapporo.

(9) PROCEEDINGS, Sixth Annual Meeting of the Tumor Marker, p.248-250, Oct. 20 (1986). Sapporo.

Since basic fetoprotein is present in the serum of cancer patients in a trace amount, it is necessary to establish a highly sensitive assay system to determine it. RIA and EIA methods have been mainly developed therefor. Detailed descriptions of the RIA method are found in the references (3) to (7) as cited above. Detailed descriptions of the EIA method are found in the following references (10) and (11).

(10) Ishii, M. et al.: Basic fetoprotein, present clinical function test—enforcement and interpretation thereof. Nippon Rinsho 37, 1536-1539 (1979).

(11) Ishii, M.: Basic fetoprotein: Rinsho Kensa 24, (8), 931-936 (1980).

Subsequently, the inventors have succeeded in obtaining monoclonal anti-basic fetoprotein antibodies. Preparation and evaluation of said monoclonal antibodies are described in the following reference (12).

(12) Ishii, M. et al.: Production of Monoclonal Anti-Basic Fetoprotein (BFP) and Usefulness of Monoclonal Anti-BFP for Immuno-diagnosis of Human Cancer, Tumor Research, Vol. 18, (Special Issue),1983 p75-86.

The reaction specificities for basic fetoprotein of the monoconal antibodies thus obtained were examined by the EIA and MO (Micro-Ouchterlony) methods. Consequently, it was found that there are at least three different antigenic determinants on the basic fetoprotein molecule and that the monoclonal antibodies might be classified into three types corresponding to each antigenic determinant. Examples of monoclonal antibodies corresponding to the three antigenic determinants A, B and C are as follows:

| antigenic determinant | monoclonal antibody |
| --- | --- |
| A | 5C4, 5C5, 5C6, 7D1, K1 |
| B | 5B3, 5C2 |
| C | 5A2, 5A3, 7D3, 8A2, 7B4, 5D6-2, 8A1, 7A5, 8A5, 7B6 |

Based on the above findings, the inventors have established a highly sensitive method for assaying basic fetoprotein in serum by a sandwich method with the use of these monoclonal antibodies (Japanese Patent Application Laying Open (KOKAI) No. 80768/1985).

However, all the assay methods referred to in the above are directed to BFP in serum. On the other hand, no evidence has been obtained up to now that BFP may be detected in urine of healthy donors or patients with various diseases.

When assayed using urine, no significant difference was obtained with respect to an amount of well known tumor markers such as carcinoembryonic antigen (CEA), AFP and the like between healthy donors and patients with cancer. Particularly a tumor marker which is useful in diagnosing urogenital cancer has not yet been found.

The present inventors have found the presence of BFP in urine of healthy donors and patients with various diseases as well, and have studied its utility as a tumor marker, leading to the perfection of the present invention.

DISCLOSURE OF INVENTION

Accordingly, it is an object of the present invention to provide an assay method, which is highly useful for diagnosing various kinds of cancers, in particular urogenital one and judging therapeutical effect thereon. The method of the present invention is characterized in that BFP in urine may be detected.

Any immunoassay method such as for example RIA and EIA methods may be used for the present method, EIA being however preferable in view of safety, sensitivity and the like.

BEST MODE FOR CARRYING OUT THE INVENTION

Figure 1:
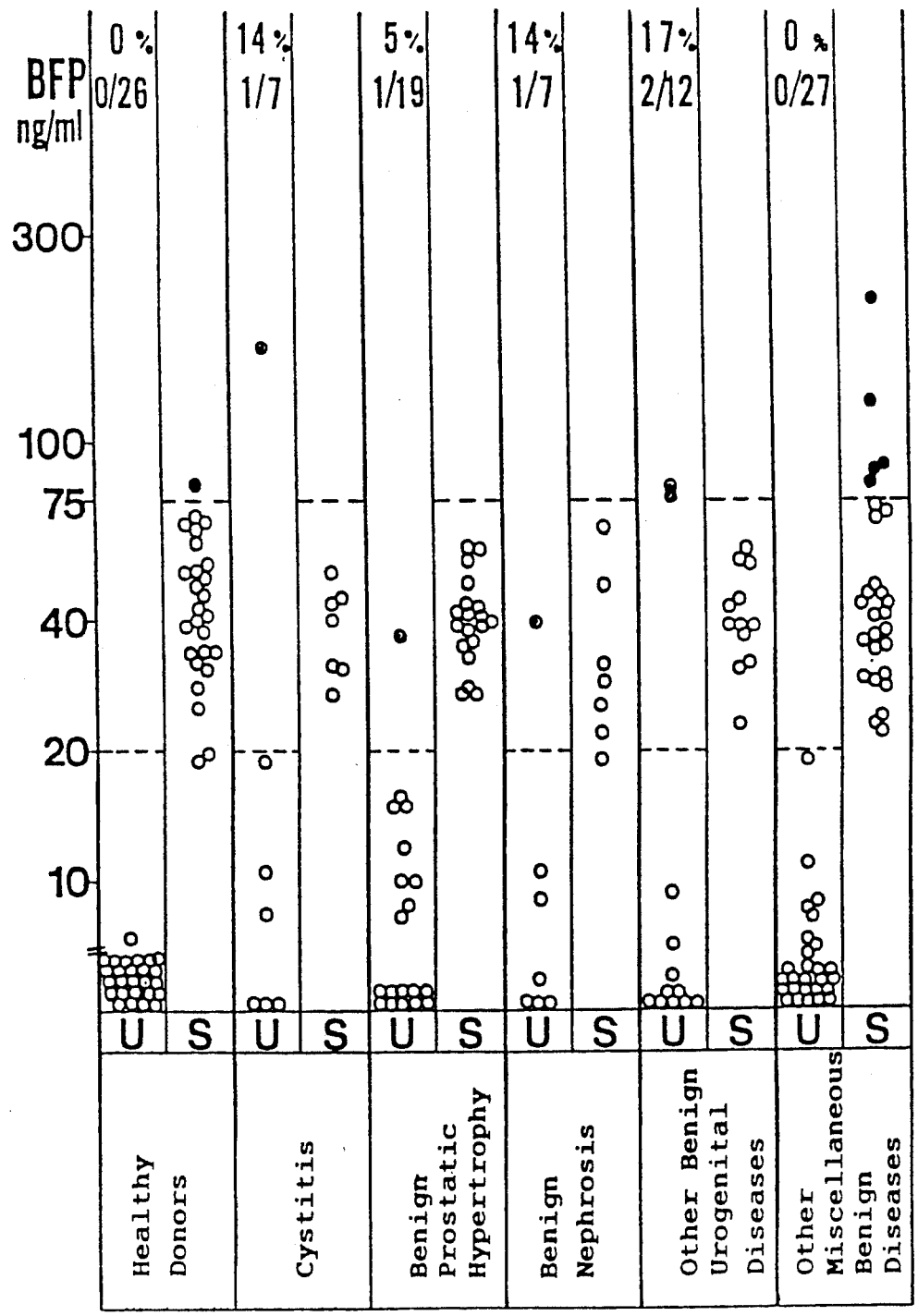
FIG. 1 shows the results obtained by assaying BFP in serum and urine of healthy donors and patients with benign urosis.

One preferable embodiment of the present invention may be a sandwich method with the use of monoclonal antibodies as a first and second antibody and carried out by taking advantage of EIA.

Now the present invention will be described in detail with reference to the above EIA (sandwich) method with the use of monoclonal antibodies.

BFP, which can be assayed by the present method, is a tumor marker with a low organ specificity as described above.

Monoclonal anti-basic fetoprotein antibodies used in the present invention may be prepared, for example, in the following manner. Antibody-forming cells obtained from a BALB/c mouse immunized with basic fetoprotein are fused with myeloma cells, P3-X63-Ag8-U1, by a variation of the method reported by Herzenberg et al. Subsequently the antibodies titer of the fused cells selected by a HAT medium was assayed by plate binding assay with the use of basic fetoprotein labeled with $^{125}I$. Some cell strains showing high antibody titers are obtained by cloning fused cells which exhibit a high antibody titer and excellent proliferation by the technique of limiting dilution. Finally each cell strain thus obtained is transplanted into the intraperitoneum of a mouse and its ascites thus obtained is fractionated with ammonium sulfate, dialyzed and subjected to DEAE-cellulose column chromatography to collect an IgG component, thereby obtaining some monoclonal antibodies available in the present invention. The monoclonal antibodies thus obtained may be classified into three types corresponding to the three antigenic determinants of BFP by the MO and EIA methods as described below.

MO Method

Mixtures of all combinations of two monoclonal antibodies at a ratio of 1:1 are prepared. Formation of a precipitation line and the presence of fusion between these mixtures and BFP are observed by the MO method. When an obvious precipitation line is observed, the monoclonal antibodies constituting the mixture are classified into different groups which react with antigenic determinants different from each other. On the other hand, when no precipitation line is observed, they belong to the same group which reacts with an antigenic determinant. When an unobvious precipitation line makes it impossible to judge definitely, the following EIA method may be employed.

EIA Method

The procedure of Example 1 is followed except that two monoclonal antibodies selected arbitarily are used instead of the K1 and 5C2 antibodies to prepare reagents of every combination of the monoclonal antibodies. Development value is determined by EIA operations. When development is observed, the monoclonal antibodies constituting the combination are classified into different groups which react with antigenic determinants different from each other. On the contrary, when no development is observed, they belong to the same group which reacts with an antigenic determinant.

Thus, the monoclonal antibodies can be classified into three groups corresponding to the three different types of antigenic determinants of BFP by the MO and EIA methods.

The whole assay system consists of a solid phase, an antibody for coating the solid phase (the first antibody), BFP (a standard antigen and test urine sample), a labeled antibody (the second antibody), an enzyme and a substrate. A well of a microtiter-plate for EIA or a plastic bead may be used as the solid phase. Prior to the assay, one of the monoclonal antibidies of the present invention is selected arbitrarily as the antibody for coating the solid phase (the first antibody), dissolved in a 0.1 M sodium carbonate buffer (pH 9.0) to give a protein concentration of $OD_{280nm}$ of 0.050, pipeted, for example, into a polystyrene well for EIA or a plastic bead and allowed to stand overnight at 4° C. to thereby coat the surface of the solid phase with the first antibody. The standard antigen may be prepared by isolating from ascites obtained from a patient with hepatoma to prepare purified BFP and diluting it to a certain concentration with a standard antigen diluent.

The labeled antibody (the second antibody) is a monoclonal antibody of the present invention which reacts with an antigenic determinant different from the one with which the first antibody reacts. Examples of available enzymes are alkali phosphatase, glucose oxidase, peroxidase and $\beta$-galactosidase. Prior to the assay, the labeled antibody may be linked to the enzyme with a conjugate agent such as glutaraldehyde to form an enzyme labeled antibody which may be used as a part of the reagent of the present invention. The substrate may be arbitrarily selected depending on the enzyme to be used. For example, p-nitrophenyl phosphate may be used when alkali phosphatase is selected as the enzyme.

The assay may be carried out in a conventional manner of EIA. Thus, as shown in Examples as described below, it may be carried out by introducing a standard antigen or test urine into a well coated with the first antibody to incubate, subsequently adding an enzyme labeled antibody (e.g. the second antibody/alkali phosphatase labeled antibody) to incubate, finally adding the substrate (e.g. p-nitrophenyl phosphate) to incubate and determinating the amount of hydrolyte of substrate with a spectrophotometer.

The first antibody used for coating the solid phase may be either a single monoclonal antibody or a mixture of several monoclonal antibodies. That is to say, it is not the determining factor in the present invention whether the first and the second antibodies consist of a single or several monoclonal antibodies so long as the first and the second antibodies react with antigenic determinants different from each other.

Although the present invention in which monoclonal antibodies are used has been described above, the antibodies usable in the present invention are not restricted to monoclonal ones, but conventional polyclonal ones may be used as well.

Another object of the present invention is to provide an assay kit for assaying BFP in urine. The assay kit comprises the first antibody, the labeled second antibody, the solid phase and the standard BFP antigen.

The present invention will be further illustrated referring to the following Example.

EXAMPLE

To 5 ml portions of mouse ascites which contained monoclonal antibodies K1and 5C2 each reacting with antigenic determinants of BFP different from each other, a saturated ammnium sulfate solution (4.05 M) was added to give a final concentration of 1.8 M and stirred for two hours at room temperature. Each mixture was centrifuged at 12,000 rpm for 20 min to thereby separate precipitate from supernatant. The precipitate was dissolved and dialyzed against the buffer solution used to dissolve the precipitate. The dialyzate was applied to a DEAE-cellulose column to elute the IgG component with a 0.1 M phosphate buffer (referred to hereinafter as "PB", pH 8.0). The eluted IgG component was concentrated by a collodion bag (MW 12,000) to prepare K1 and 5C2. The K1was dissolved in a 0.1 M sodium carbonate (pH 9.0) to give a protein concentration of $OD_{280nm}$ of 0.05 and the solution was poured into a well of a microtiter plate for EIA and allowed to stand overnight. After removing the liquid, the residue was washed with 0.1 M sodium carbonate (pH 9.0) and dried by a well drier to prepare a solid phase first antibody.

On the other hand, the enzyme labeled antibody may be prepared in the following manner.

Horseradish peroxidase was dissolved in 0.1 M PB (pH 6.8) containing 1.25% of glutaraldehyde, allowed to react for 20 hours at room temperature and dialyzed against physiological saline. With this dialyzate a solution of the monoclonal anti-BFP antibody 5C2, which had been dialyzed against physiological saline, was mixed at a ratio of 1:1 by volume. To this mixture 1 M carbonate buffer (pH 9.5) was added to a final concentration of 5% and allowed to stand for 24 hours at 4° C. After adding 0.2 M of lysine solution to a final concentration of 5%, the resulting mixture was allowed to stand for 2 hours at room temperature and dialyzed against physiological saline and then against 0.05 M PB (pH 7.4) to give a horseradish peroxidase labeled anti-BFP antibody.

Separately, a reaction diluent, a developer solution, a reaction stopper solution and a standard antigen diluent were prepared in the following manner.

Normal calf serum, normal mouse serum (inactivated at 56° C. for 30 min.), EDTA 3Na, sodium chloride and sodium azide were added to a 0.05 M tris hydrochloride buffer solution (pH 8.0) to give concentrations of 11.8%, 2%, 10 mM, 0.15 M and 0.1%, respectively, to thereby prepare a reaction diluent.

2,2'-azinobis(3-ethylbenzothiazoline-6-sulfonic acid) di-ammonium (ABTS) was added to a 0.1 M citrate buffer solution (pH 4.0) to give a concentration of 3 mg/ml, to which hydrogen peroxide was added to a final concentration of 0.02 % to thereby prepare a developer solution.

A 0.1 M citrate buffer solution containing 0.01% of sodium azide was prepared as a reaction stopper solution.

Normal calf serum (inactivated at 56° C. for 30 min.), EDTA 3Na, sodium chloride and sodium azide were added to a 0.05 M tris hydrochloride buffer solution (pH 8.0) to give concentrations of 18.1%, 10 mM and 0.1%, respectively, to thereby prepare a standard antigen diluent.

A specimen and a standard antigen having a known concentration were diluted 11-fold with a reaction diluent and poured into wells which had been previously washed in 100 μl portions and incubated for one hour at 37° C. After washing with physiological saline, 100 μl of an enzyme labeled antibody of the proper concentration was added and incubated for one hour at 37° C. After rewashing with phisiological saline, 100 μl of a developer solution was added and incubated for one hour at 37° C. Subsequently 100 μl of a 0.01% sodium azide solution was added to stop the reaction and the optical density was determinated at 420 nm $OD_{420nm}$) to calculate the BFP value.

A total number of the specimen used in this assay is 142, consisting of 26 specimen of healthy donors, 45 specimen of benign urosis patients, 27 specimen of the other miscellaneous benign desease patients, 27 specimen of urogenital cancer patients, 6 specimen of the other miscellaneous cancer patients and 11 specimen of recurrent urogenital cancer patients. Urine specimen were collected upon occasion and stored after an addition of sodium azide at 4° C. Serum specimen were obtained from the same donors at the same time as of urine specimen.

A mean value of BFP in urine of 26 healthy donors was calculated to be 2.6 ng/ml, the mean value+2SD being 7.3 ng/ml. Considering the value obtained from benign disease and cancer patients, 20 ng/ml was adopted as a cut-off value. On the other hand, a cut-off value for serum specimen was determined to be 75 ng/ml.

Figure 2:
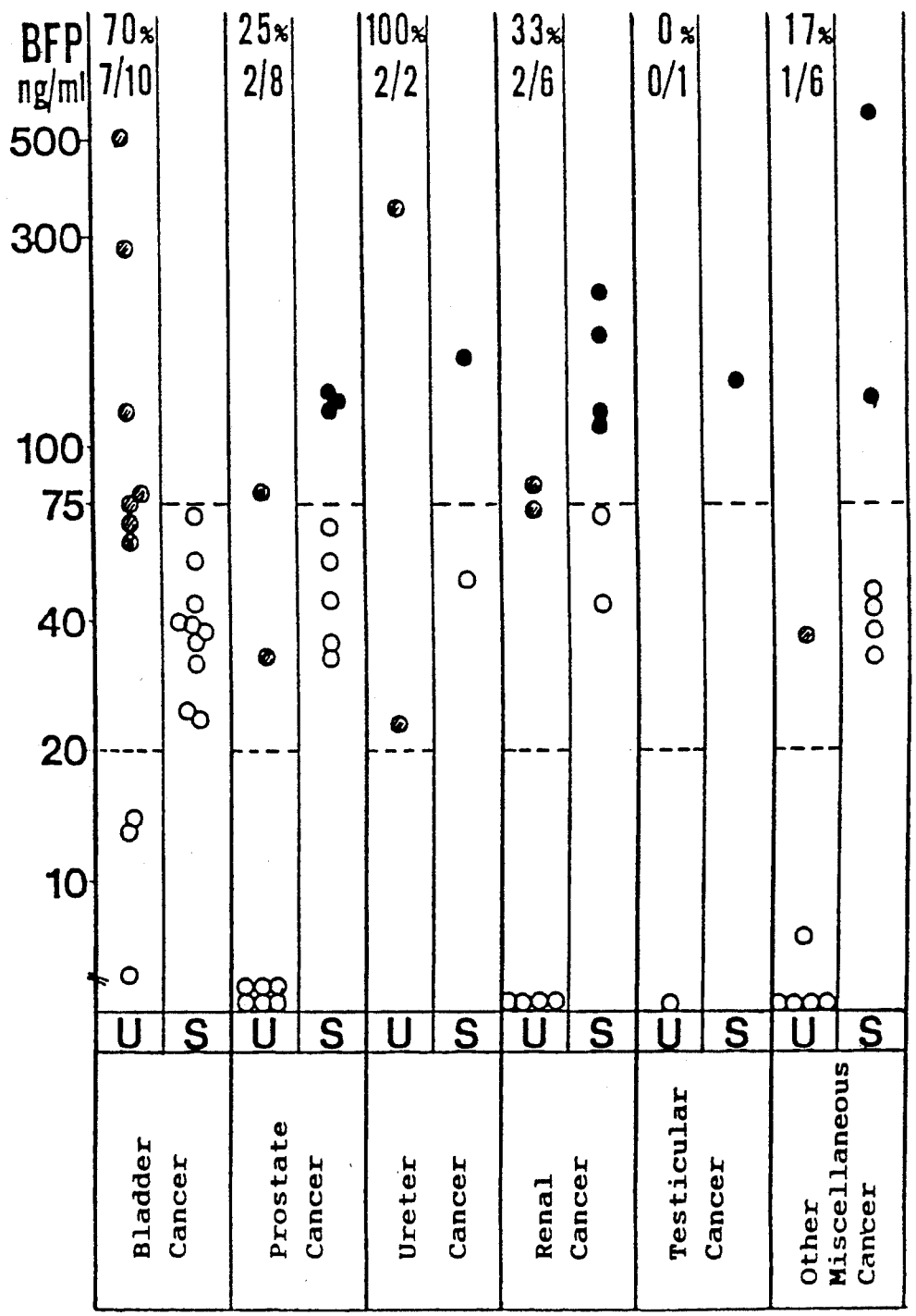
FIG. 2 shows the results obtained by assaying BFP in serum and urine of patients with urogenital cancers.

Positive percentages of urine BFP and serum BFP of each patient group are as follows: 11% and 0% for benign urosis patients; 0% and 18.5% for the other miscellaneous benign disease patients; 48% and 33% for urogenital cancer patients; 17% and 33% for the other miscellaneous cancer patients; 27% and 25% for recurrent urogenital cancer patients, respectively. The details of the positive percentages of urine BFP for urogenital cancer patients are as follows: bladder cancer 70% (7/10); ureter cancer 100% (2/2); prostate cancer 25% (2/8); renal cancer 33% (2/6); testicular cancer 0% (0/1), indicating that significantly high positive percentages were obtained particularly with respect to urine BFP in urinary tract cancers such as bladder cancer and ureter cancer when compared to serum BFP. Such results are shown in FIG. 1 and FIG. 2, in which U and S represent urine BFP and serum BFP, respectively.

No correlation was found between the urine BFP value and the serum BFP value. The combination assay of urine BFP and serum BFP could increase a positive percentage for urogenital cancer upto 70%, the details of which are 83% (5/6) for renal cancer, 50% (4/8) for prostate cancer and 100% (1/1) for testicular cancer.

An influence of hematuria on the BFP value was examined. No correlation was seen between the urine BFP value and a number of erythrocyte in urinary sediment. The urine BFP values of cystitis and benign prostatic hypertrophy with hematuria were 164.7 ng/ml and 14.9 ng/ml, respectively.

INDUSTRIAL APPLICABILITY

A high positive percentage was obtained with respect to the urine BFP of urogenital cancer pateints, particularly of bladder cancer and ureter cancer, indicating that BFP may serve as a tumor marker which is highly specific against these cancers. Furthermore, the combination assay of urine BFP and serum BFP could significantly increase the positive percentages for renal cancer and prostate cancer so that a high utility of this assay in diagnosis of urinary organ has been proved.

As seen from the above description, the present method may provide very useful data in screening of cancer, particularly urogenital cancer, its diagnosis and judgement of therapeutical effect thereon.

We claim:

1. A method for detecting the presence of urogenital cancer in an individual, wherein the method comprises:
   contacting a urine sample from the individual with at least one antibody which specifically binds basic fetoprotein,
   detecting formation of an immune complex between the antibody and basic fetoprotein and determining the amount of basic fetoprotein in the urine sample, wherein an elevated level of basic fetoprotein is associated with the presence of urogenital cancer.

2. A method according to claim 1, wherein said method is carried out by a sandwich assay.

3. A method according to claim 2, wherein said method is carried out by a sandwich assay using a first monoclonal antibody that specifically binds basic fetoprotein and a labeled second monoclonal antibody that specifically bids basic fetoprotein and which reacts with an antigenic determinant different from the antigenic determinant with which said first monoclonal antibody reacts.

4. A method according to claim 3, wherein the first monoclonal antibody is coated on a surface of a solid phase.

5. A method according to claim 3 or 4, wherein the second monoclonal antibody is labeled with an enzyme.

* * * * *